United States Patent
Babaeizadeh et al.

(10) Patent No.: US 8,560,058 B2
(45) Date of Patent: Oct. 15, 2013

(54) REAL TIME ATRIAL FIBRILLATION MONITORING

(75) Inventors: Saeed Babaeizadeh, Brookline, MA (US); Richard E. Gregg, Westford, MA (US); Eric Helfenbein, Sunnyvale, CA (US); Sophia Huai Zhou, Camarillo, CA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 12/811,841

(22) PCT Filed: Jan. 9, 2009

(86) PCT No.: PCT/IB2009/050089
§ 371 (c)(1),
(2), (4) Date: May 13, 2011

(87) PCT Pub. No.: WO2009/090581
PCT Pub. Date: Jul. 23, 2009

(65) Prior Publication Data
US 2011/0208079 A1    Aug. 25, 2011

Related U.S. Application Data

(60) Provisional application No. 61/020,796, filed on Jan. 14, 2008, provisional application No. 61/097,932, filed on Sep. 18, 2008.

(51) Int. Cl.
*A61B 5/0402* (2006.01)
(52) U.S. Cl.
USPC .......................................................... 600/518

(58) Field of Classification Search
USPC .......................................... 600/509, 518–519
See application file for complete search history.

(56) References Cited

U.S. PATENT DOCUMENTS

| 6,615,075 B2 | 9/2003 | Mlynash et al. |
| 6,937,887 B2 * | 8/2005 | Bock .............................. 600/519 |
| 2003/0144597 A1 | 7/2003 | Bock |
| 2006/0084881 A1 | 4/2006 | Korzinov et al. |
| 2006/0200036 A1 | 9/2006 | Kurzweil et al. |
| 2006/0276716 A1 | 12/2006 | Healey et al. |

FOREIGN PATENT DOCUMENTS

WO    2008/007236 A    1/2008

OTHER PUBLICATIONS

Babaeizadeh, S., et al., "Monitor atrial fibrillation burden using a miniaturized electrocardiographic recorder," Journal of Electrocardiology, XX, XX, vol. 41, No. 6, Nov. 1, 2008, pp. 636-637, XP025622939.

Battle, X. L., et al., "3D Tomographic Reconstruction Using Geometrical Models," Medical Imaging: Image Processing, Proc. SPIE 3034, (1997), pp. 346-357, XP007908723.

(Continued)

*Primary Examiner* — Scott Getzow
*Assistant Examiner* — Amanda Patton

(57) ABSTRACT

An atrial fibrillation (AF) monitor extracts two P wave features and an R-R interval feature from a sequence of ECG waveforms. The features are used by a classifier to classify a heart rhythm as AF or non-AF. The AF classification results may be further processed to reduce false alarm reporting. The AF classification results are used by an AF burden calculator to report AF burden in real time.

13 Claims, 9 Drawing Sheets

(56) References Cited

OTHER PUBLICATIONS

Soussen, C., et al., "Contour-based models for 3D binary reconstruction in X-ray tomography," Bayesian Inference and Maximum Entropy Methods in Science and Engineering: 20th International Workshop, American Institute of Physics, 2001, pp. 543-554, XP007908746.

Soussen, C., et al., "Polygonal and Polyhedral Contour Reconstruction in Computed Tomography," IEEE Transactions on Image Processing, vol. 13, No. 11, Nov. 2004, pp. 1507-1523, XP11120320.

Sitek, A., et al., "Tomographic Reconstruction Using an Adaptive Tetrahedral Mesh Defined by a Point Cloud," IEEE Transactions on Medical Imaging, vol. 25, No. 9, Sep. 2006, pp. 1172-1179, XP007908724.

Amit, G., et al., "Detection of acute myocardial ischemia using high-frequency QRS analysis," Journal of Electrocardiology, 41, (2008), pp. 636-641, www.sciencedirect.com or www.jecgonline.com.

* cited by examiner

REAL TIME ATRIAL FIBRILLATION MONITORING

This invention relates to electrocardiogram (ECG) monitoring systems and, in particular, to EGG monitoring systems which monitor for indications of atrial fibrillation in real time.

Atrial fibrillation (AF) is an arrhythmia where the atria do not contract in an organized fashion along with the rest of the heart to pump blood efficiently. The atria quiver or fibrillate at a very high irregular rate and therefore the ventricles also beat in an irregular rate. The atrial "kick" during each heartbeat is lost and the pumping efficiency of the heart is reduced. Since the atria do not contract significantly during fibrillation, blood can pool in the atria and blood clots can develop. Although atrial fibrillation generally does not cause death itself, a large proportion of all strokes are attributable to blood clots formed during AF. AF occurs in approximately 0.4% to 1.0% of the general population, and affects more than 2 million people in the United States annually. The prevalence of AF increases with age, and up to 10% of the population older than 80 years is diagnosed with AF at some point in time. Stroke is the third largest killer in North America behind only heart attacks and cancer. In addition, patients often exhibit symptoms such as sudden episodes of palpitations and shortness of breath. Thus, atrial fibrillation is a serious condition that demands treatment.

Systems and algorithms have been developed for identifying symptoms of AF from the ECG waveforms of patients. Two such techniques are described in U.S. Pat. Nos. 6,490,479 and 6,937,887, for instance. However, available AF detection algorithms are sometimes unable to specify AF over some other arrhythmias. This misclassification of other irregular rhythms as AF results in false alarms. Since clinical staff must respond to and validate each and every alarm, it is desirable to reduce the number of false alarms as much as possible. Too many false alarms mean additional work, for the clinical staff which may reduce alarm sensitivity to reduce false alarms, which inherently desensitizes them to true alarms. For example, an AF monitoring system should include a method to distinguish between AF which has an irregularly irregular rhythm and an arrhythmia with regularly irregular rhythm such as atrial bigeminy, which is commonly mistaken as AF by known methods.

Known AF detection algorithms, in general, only make a binary decision, meaning they classify a rhythm as either AF or non-AF. It would be desirable to not only identify AF, but provide a measure of the confidence that the identifies rhythm is AF. Such a confidence measure would assist the clinical staff in evaluating the severity of an AF alarm.

Known algorithms only alarm when an AF episode begins. Sometimes it is as important to alarm when AF ends. For example, medical staffs are interested in knowing when AF ends for patients who are being cardioverted or treated with drugs. It is thus desirable for an AF monitor to alert the medical staff when an AF episode ends in addition to when the AF episode begins.

Currently, there is no clear consensus on optimal endpoints for defining responses to AF therapy. Therefore, endpoints which react adequately and represent a positive or negative therapy effect are needed. Such endpoints should be able to guide therapies which target complete cure of AF, such as left atrial ablation procedures, as well as those therapies which aim at reducing symptomatic AF episodes and enhancing quality of life, such as pharmacologic therapies. A monitoring system which reports real-time AF burden would help guide a medical staff in evaluating the need for and effectiveness of different therapies.

Furthermore, many AF monitoring techniques do not have the facilities to take into account the type of AF monitoring which is needed for a particular disease condition. For example, patients with chronic or permanent AF, patients who have been recently cardioverted, and patients with paroxysmal AF can have differing monitoring needs. Whether there is a need to know instantly about a rhythm change or just long-term trending, the monitor alarm should be configurable for the needs of the particular patient.

In accordance with the principles of the present invention, an atrial fibrillation monitoring system detects AF and reports AF burden in real time. In the exemplary monitoring system describe below, a beat classifier selects those beats of the input ECG signal which fit the criteria being used for AF detection. Selected beats are combined to generate a P wave template beat. Analysis of the template identifies a P wave feature and an R-R interval feature is also identified. A feature vector is computed using at lease one P wave feature and an R-R interval feature. A classifier, which is a set of rules, is used to classify the feature vector as either AF or non-AF. AF classifications are examined using a second set of rules to correct possible misclassification. The inventive technique may optionally provide a confidence measure for its AF detection. The system can calculate and report real-time AF burden at any point in time defined by frequency and duration of AF episodes. The system may tailor its AF monitoring to the patient by taking into account the patient characteristics which drive the monitoring requirement.

Figure 1:
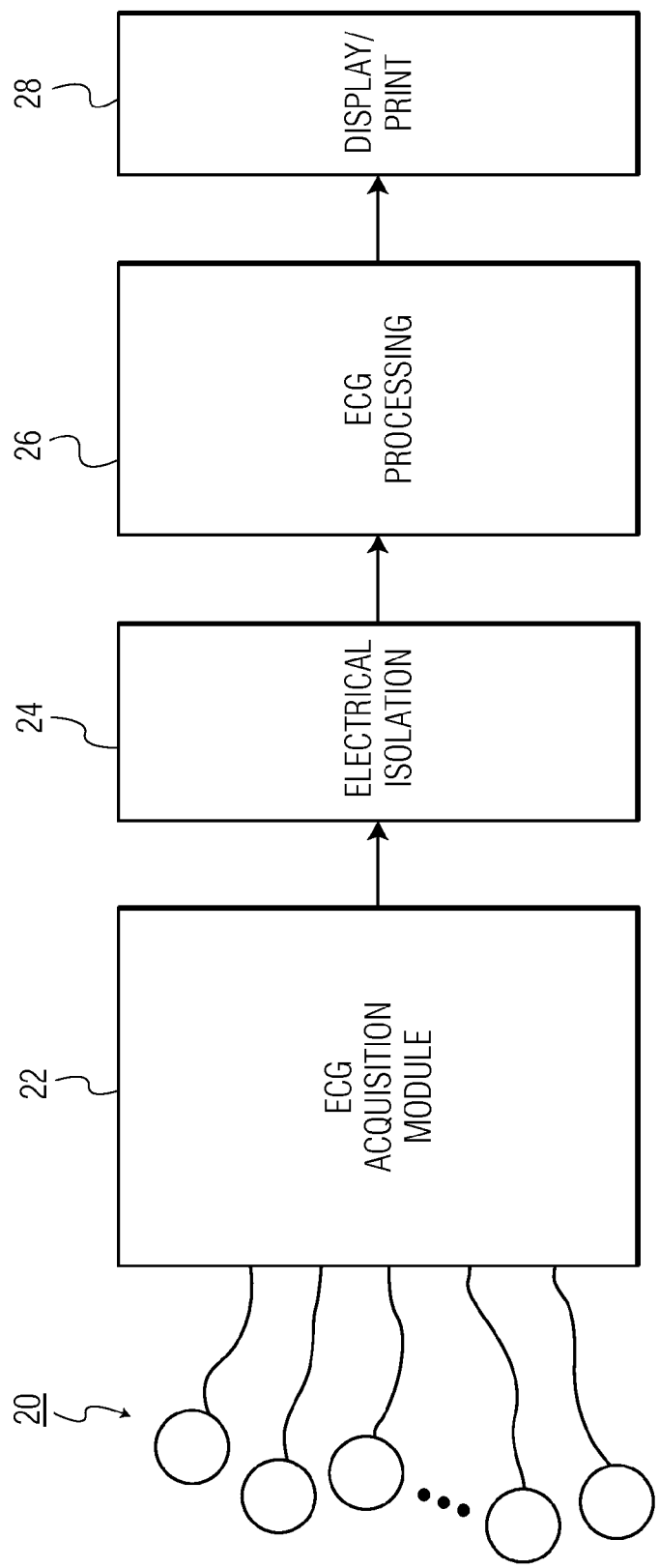
FIG. 1 is a block diagram of the major subsystems of an ECG monitoring system.

FIG. 1 illustrates in block diagram form the major subsystems of an ECG monitoring system suitable for use with the present invention. A plurality of electrodes 20 are provided for attaching to the skin of a patient. Usually the electrodes are disposable conductors with a conductive adhesive gel surface that sticks to the skin. Each conductor has a snap or clip that snaps or clips onto an electrode wire of the ECG system. The electrodes 20 are coupled to an ECG acquisition module 22 that preconditions the signals received by the electrodes. The electrode signals are coupled to an ECG processing module 26, generally by means of an electrical isolation arrangement 24 that protects the patient from shock hazards and also protects the ECG system when the patient is undergoing defibrillation, for instance. Optical isolators are generally used for electrical isolation. The processed ECG information is then displayed on an image display or printed in an ECG report by an output device 28.

Figure 2:
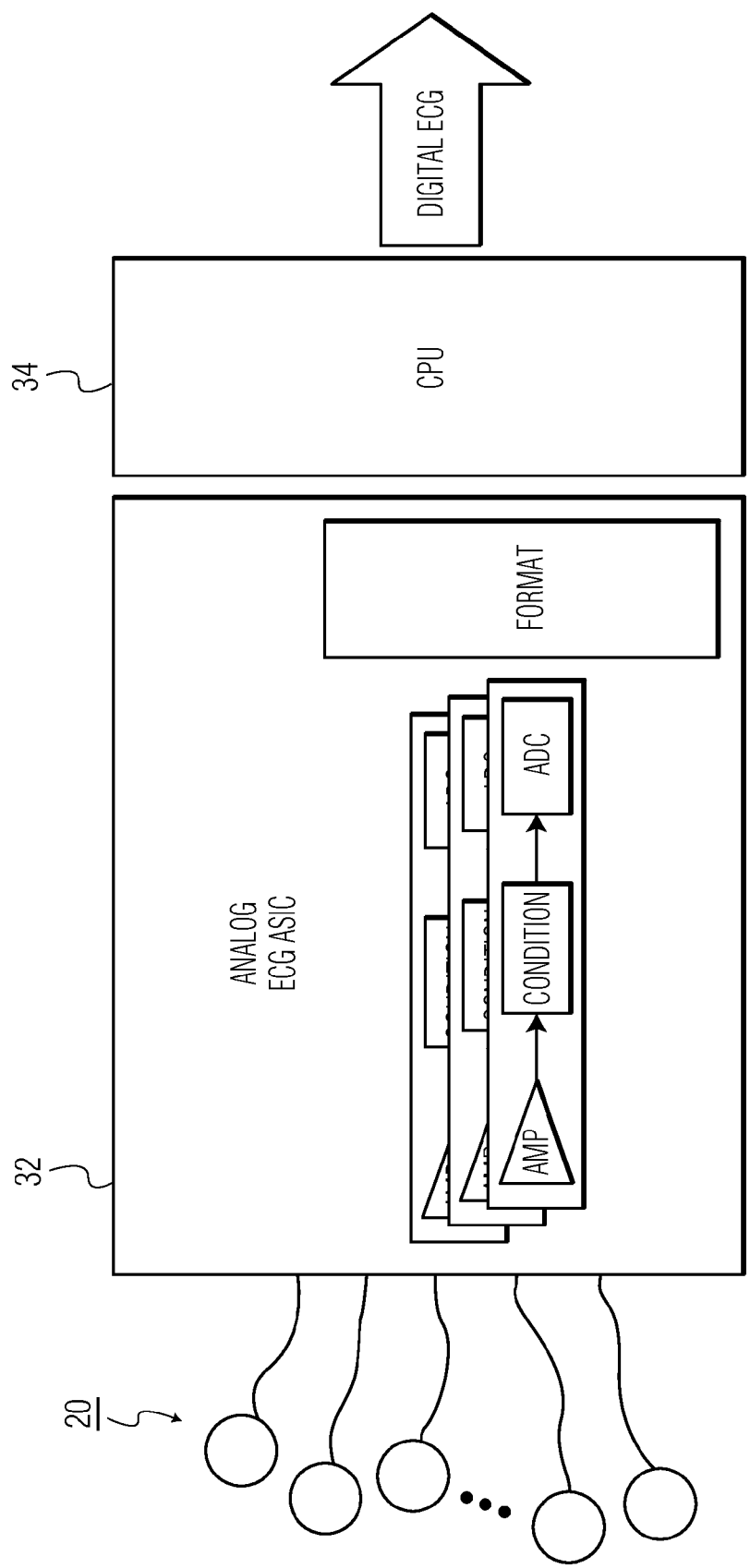
FIG. 2 is a block diagram of the front end of an ECG system.

FIG. 2 shows the acquisition module 22 in greater detail. The electrode signals, which are usually just a few millivolts in amplitude, are amplified by amplifiers which also usually have high voltage protection from defibrillation pulses. The amplified signals are conditioned as by filtering and then converted to digitally sampled signals by analog to digital converters. The digital signals are forwarded for ECG processing under control of CPU 34. Much of the specialized electronics of the acquisition module can be implemented in the form of an application-specific integrated circuit (ASIC).

Figure 3:
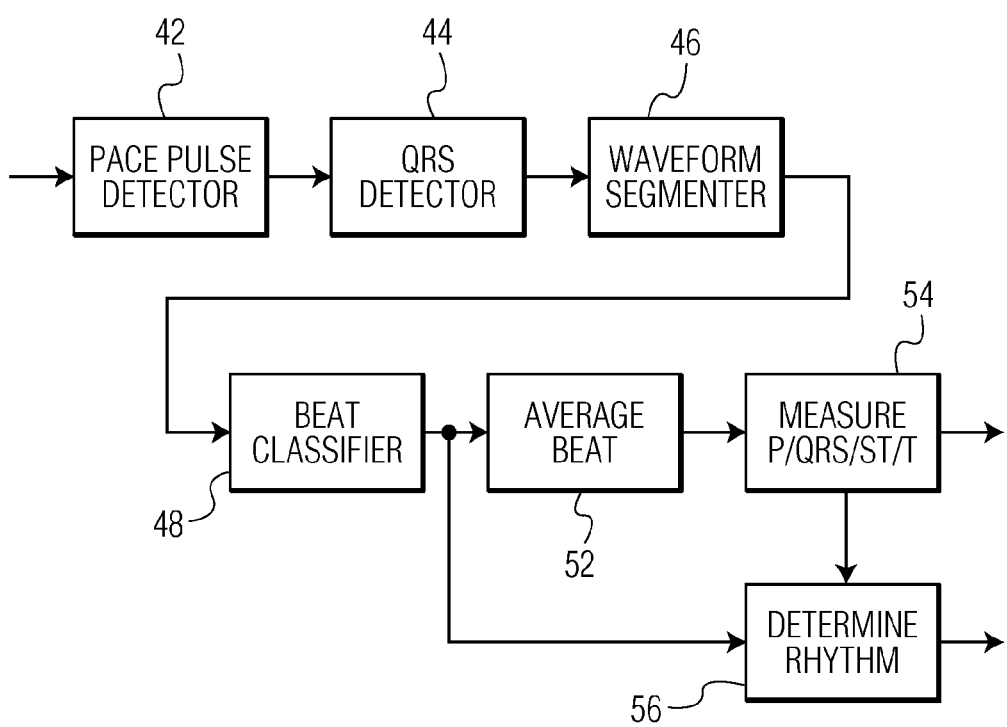
FIG. 3 is a block diagram of the processing module of a typical ECG monitoring system.
Figure 4:
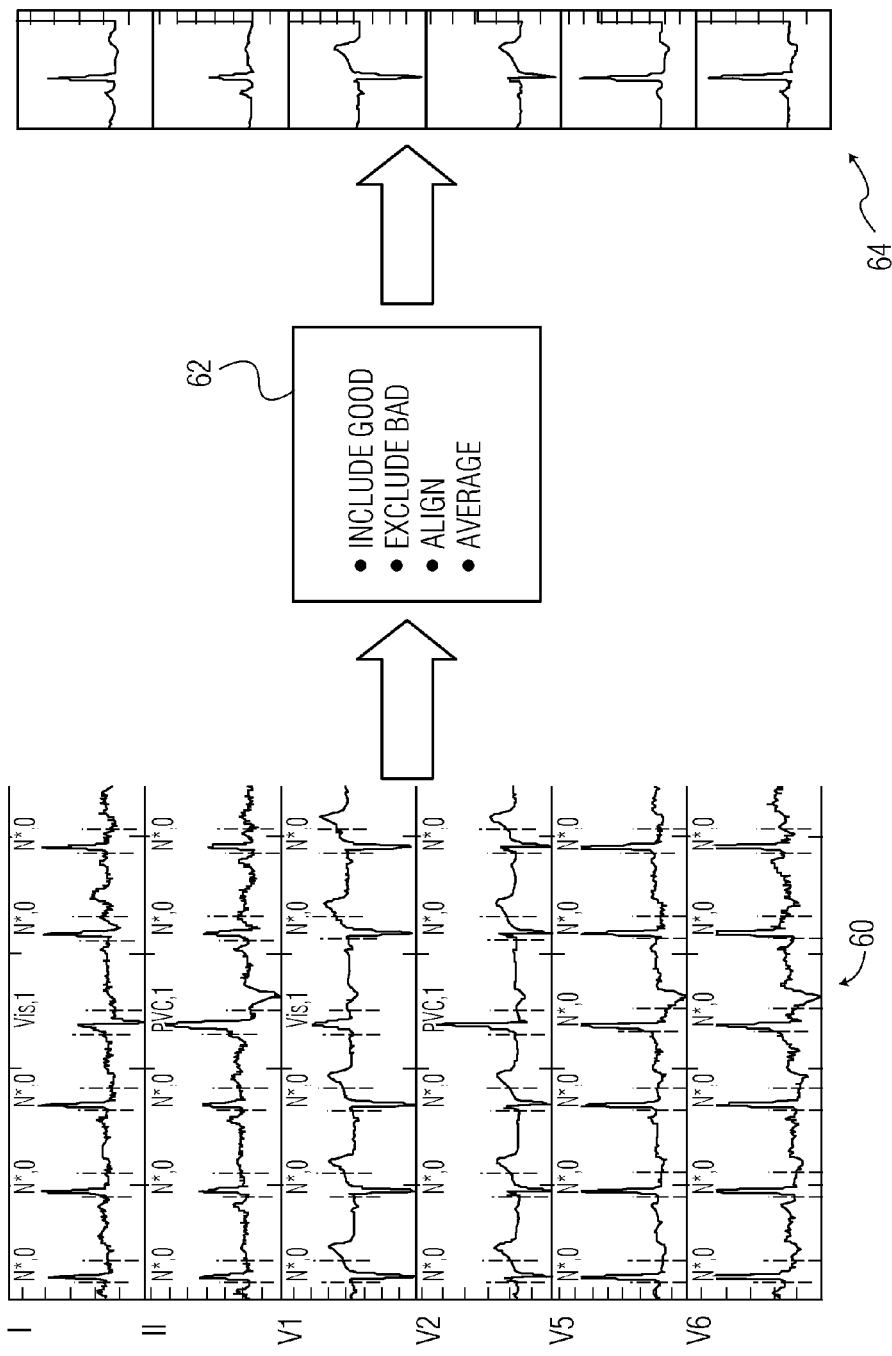
FIG. 4 illustrates the processing of ECG trace data to provide an ECG template of a plurality of heartbeats.
Figure 5:
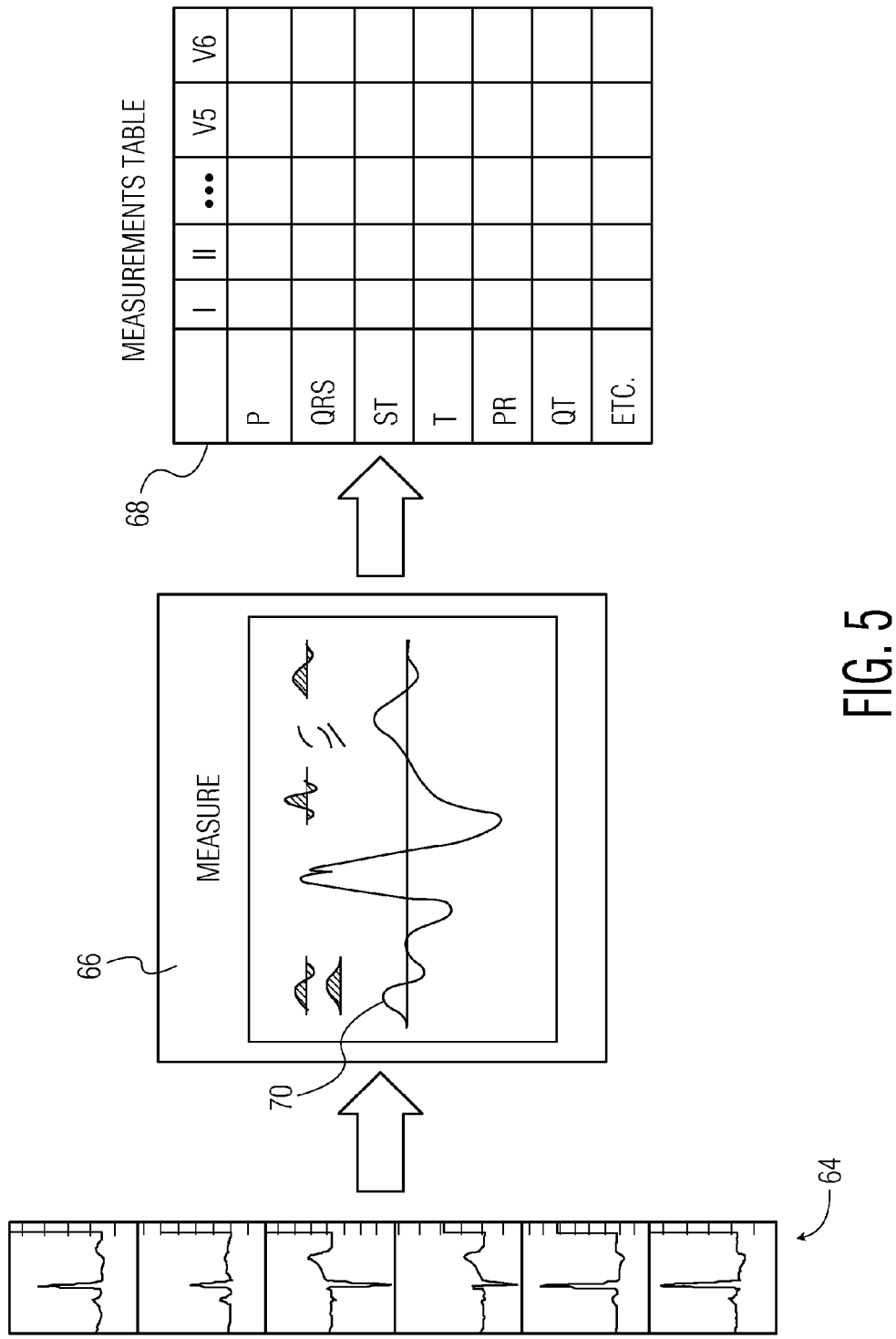
FIG. 5 illustrates the measurement of different parameters of an ECG waveform.

FIG. 3 is a block diagram of the analysis portion of a typical ECG monitoring system. A pace pulse detector 42 identifies and sets aside electrical spikes arid other electrical abnormalities produced by a pacemaker for patients who are wearing one. A QRS detector 44 detects the dominant pulse of the electrical traces. The Q-R-S segments of a normal ECG trace delineate the major electrical pulse of the trace, which is the pulse that stimulates a contraction of the left ventricle. Delineation of the QRS complex forms the basis for detecting the lesser perturbations of the trace, which is performed by the waveform segmenter 46. The waveform segmenter delineates the full sequence of trace segments including the P wave and the Q to U segments of the ECG trace. With each waveform now fully delineated, a beat classifier 48 compares each new beat with previous beats and classifies beats as normal (regular) for the individual or abnormal (irregular). The classification of the beats enables an average beat analyzer 52 to define the characteristics of a normal heartbeat and the amplitudes and segment durations of an average beat are measured at 54. The beat classifications and two P wave measurements are used to determine the heart rhythm at 56. FIGS. 4 and 5 are functional illustrations of this ECG trace processing. At the left side or FIG. 4 is a series 60 of heartbeat traces. While this drawing shows the signals of six leads, in a constructed embodiment only the main three ECG leads are used. The beat classifier 48 compares the various beat characteristics and has classified some of the beats as normal (N*,0). For example, all of the beats from leads V5 and V6 have been classified as normal in this example. The other four leads contain a beat exhibiting the characteristics of premature ventricular contraction (PVC,1; Vis,1). At 62 the ECG system aggregates the characteristics of the normal beats, excludes characteristics of the abnormal beats, aligns the beats in time and averages them to produce an average beat. The traces at 64 illustrate the traces of an average beat for the six leads shown in this example. In FIG. 5 the average beat traces 64 of the six leads are measured for various characteristics shown at 66, such as the amplitudes and durations of the P wave 70, the Q wave, the R wave, and the T wave and inter-wave intervals such as QRS duration and the P-Q interval. The measurements are illustrated as recorded in a measurement table 68 for the six leads of this example.

Figure 7:
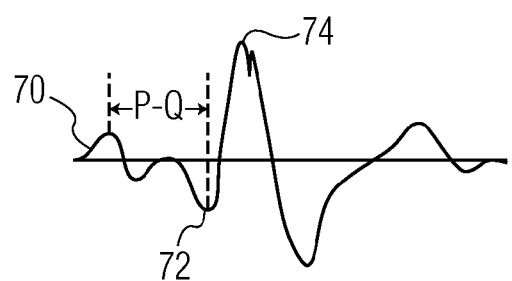
FIG. 7 illustrates a measure of P wave location.
Figure 8:
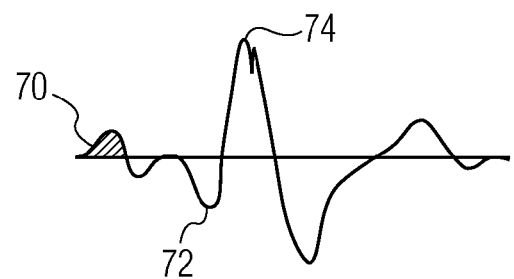
FIG. 8 illustrates a measure of P wave morphology.

The ECG waves and their measurements can be sent to an offline workstation with a report generation package for the production of a report on the patient's ECG waveforms. However most ECG monitoring systems such as the Philips IntelliVue®; monitoring system and the Philips MRx defibrillator/monitoring system have onboard ECG monitoring packages. In accordance with the principles of the present invention, an ECG monitoring system includes an atrial fibrillation detection and analysis system shown in block diagram form in FIG. 6. The beat classifier 48 provides P wave template information and R-R interval information to a P wave feature extraction processor 82 and an R-R feature extraction processor 84. Atrial fibrillation is thereby detected based on a combination of R-R interval features and P wave features. In a constructed embodiment the P wave template is compiled from selected beats in a time window. The P waves of the plurality of beats are used, to calculate a sum of absolute values of differences in the P wave waveforms of all of the leads of the selected beats in the time window. This calculated P wave template is then used in the preferred embodiment to extract a P wave location feature and a P wave morphology feature. A preferred P wave location feature is the measure of the deviation in time from the average P-Q interval, which is the time interval from the peak P wave activity to the onset of the QRS complex as shown in FIG. 7. Suitable intervals which may be used are the time from the peak of the P wave 70 to the (negative) peak of the Q wave 72, which is denoted as interval P-Q in FIG. 7. Another measure is the time from the time of the P wave 70 to the time of the R wave 74. For normal sinus rhythm the P-Q interval variation will be very small. For AF conditions the P-Q interval variation will be greater as the P wave template will not exhibit a consistently identifiable P wave. A preferred P wave morphology feature is the similarity of the P wave from template to template. Characteristics of the P wave which may be used in morphology analysis include the peak P wave amplitude, its time duration, its slope, or its area in reference to a baseline as shown by the shaded area under the P wave 70 in FIG. 8. For normal sinus rhythm the P wave characteristics will closely match from template to template. When AF is present the match of template characteristics will be poor.

A preferred R-R interval measure for AF detection is the regularity of the heartbeat. A regular R-R interval is characteristic of a normal sinus rhythm and irregular R-R intervals are characteristic of AF. A Markov model using the R-R interval data may be used to score the regularity of the R-R intervals.

A noise estimator 80 is used to compute an estimate of the noise artifacts in the ECG signal. A preferred noise measure is the sum of the second derivative of signal samples in the P wave region measured for every heartbeat. This measure is applied to the P wave extraction processor 62 and the R-R feature extraction processor 84 to inhibit feature extraction under high noise conditions.

When the noise level is sufficiently low for feature extraction, the extracted P wave and R-R interval features are applied to an AF classifier 90. The extracted features are combined by the classifier to form a feature vector which is used to classify the rhythm as either AF or non-AF. For example, the foregoing P wave and R-R interval features may be combined to identify AF by AF=[(irregular rhythm) AND (no P wave OR irregular P-R interval OR poor P wave template match)]

In a constructed embodiment the classifier also provides a confidence measure of its determination. Expert data of ECG waveforms of patients with known AF and non-AF rhythms were applied to the feature extractors 82 and 84 and also to the classifier 90 to observe the responses of the extractors to known rhythm conditions. Each feature extraction of an unverified rhythm can then be scored against these known conditions and to determine a likelihood of each feature being characteristic of AF. The combined scores are presented to the operator to provide a confidence measure of the results of classification by the classifier 90.

Figure 9:
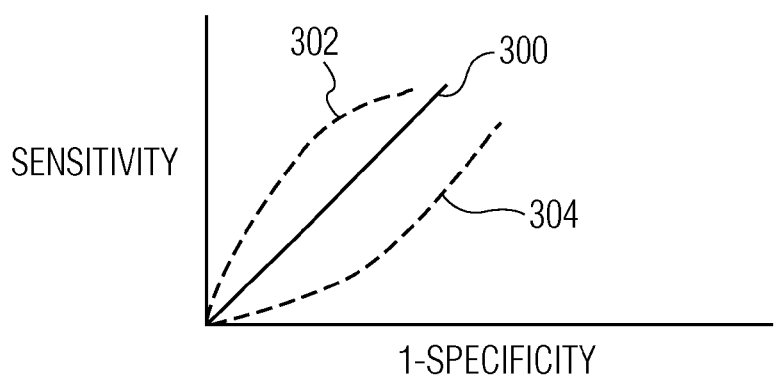
FIG. 9 illustrates a receiver sensitivity curve for adjustable AF detection sensitivity.

The use of such expert data of known patient populations to "train" the system enables the sensitivity/specificity tradeoffs to be determined for different system setups for the different patient populations. FIG. 9 illustrates ranges of receiver operating characteristics for which an atrial fibrillation detection system may be pre-conditioned. When sensitivity and its complement 1-specificity are balanced, the curve is neutral as illustrated by curve 300. If the system is set up to have greater sensitivity to AF (examples of which are given below) it will exhibit an operating characteristic weighted toward sensitivity as shown by curve 302, and if the system is set up to have greater specificity the operating curve will range as shown by curve 304. Furthermore, with the training of the system, through known patient populations, user controls can be simplified by allowing the user to select a patient population rather than go through the detail of setting numerous parameter settings. The selection of a particular patient population, e.g., "Post-cardioversion" or "Chronic AF," can result in automatic setup of the system for the nominal setup parameters desired for that particular population. For instance, patients with chronic or permanent AF may not need an alarm, but only trending of the rate and rhythm and calculation of AF burden. Patients who have been cardioverted out of atrial fibrillation need sensitive AF detection so that the medical staff will immediately know when the patient has lapsed back into AF. Cardiac surgery patients also fall into this category of patients for whom sensitive AF detection is needed to immediately alert the medical staff of a rhythm change either into or out of AF. For patients with a history of paroxysmal AF who are expected to lapse into and out of AF, less sensitive detection is desirable. If there is a need to know about a rhythm change, the alarm should be as accurate as possible trading off sensitivity for a lower false alarm rate. Short burst of AF are not important for this group. By adjusting the sensitivity/specificity balance, preferably by simply selecting a patient population type, an AF monitor of the present invention is made configurable in terms of how long and how frequently it should see AF episodes before it generates an "AF Begin" alarm, and similarly, how long and how frequently it should see non-AF episodes before it generates an "AF End" alarm. In addition to control over the minimum rhythm duration and frequency, similar control over system parameters can be used to favor a highly sensitive detection of AF (with a reduction in specificity and an increase in false alarm rate) or highly specific detection of AF (with a reduction in sensitivity).

Figure 6:
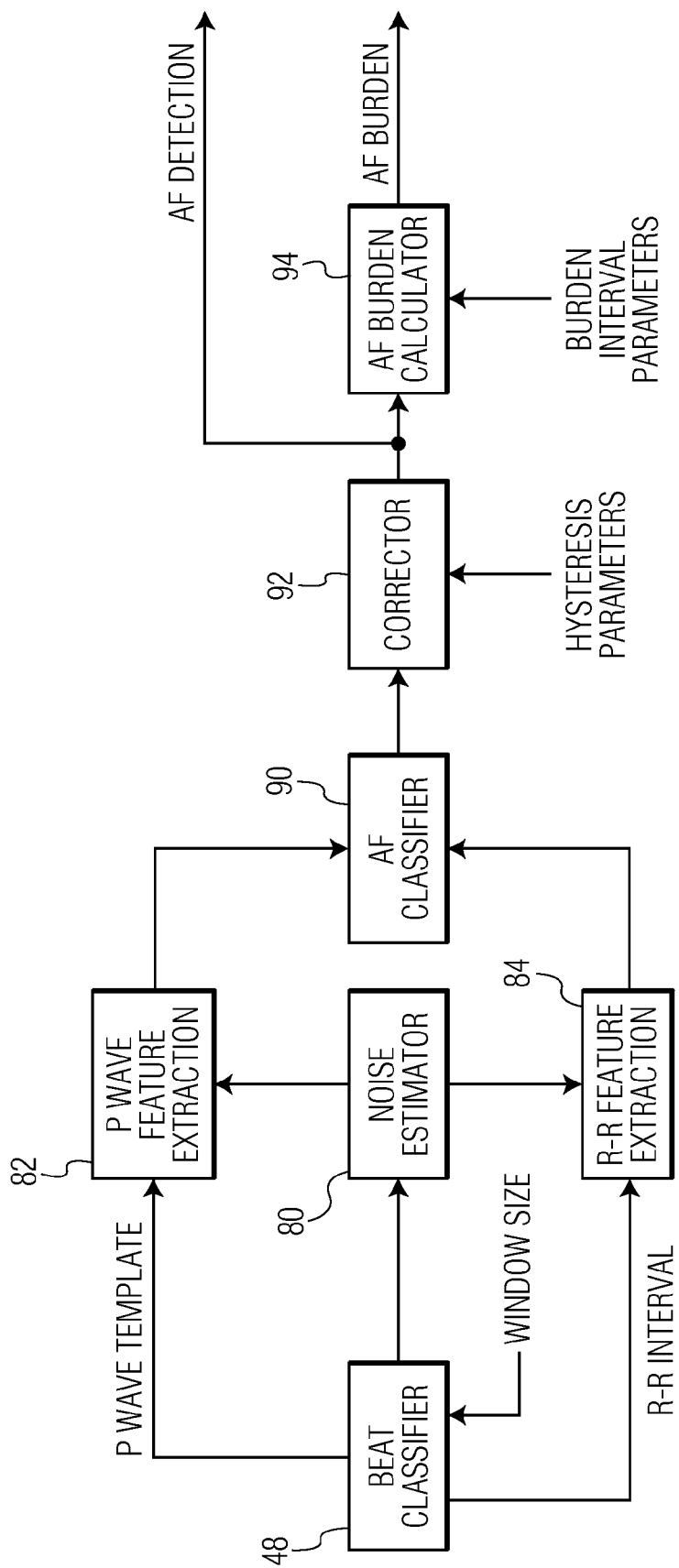
FIG. 6 illustrates an atrial fibrillation detection and analysis system constructed in accordance with the principles of the present invention.
Figure 10A:
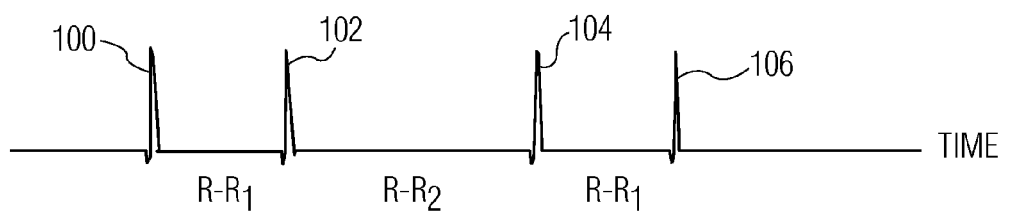
FIG. 10a illustrates regular irregular R-R intervals.
Figure 10B:
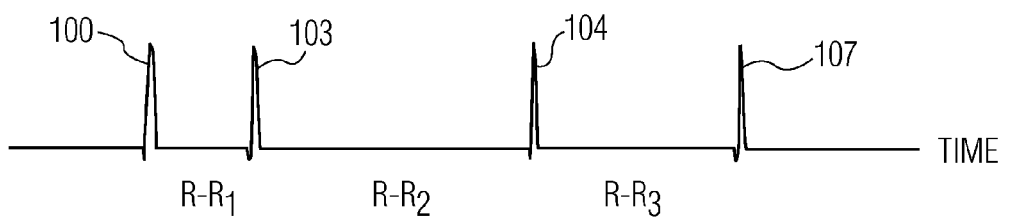
FIG. 10b illustrates irregular irregular R-R intervals.

To reduce the possibility of false alarms, the example of FIG. 6 includes a corrector 92 to reclassify those feature vectors erroneously classified as AF by the classifier 90. A variety of reclassification criteria may be used as desired. For instance, if a good P wave is present based on the P wave feature or features, a feature vector should be classified as non-AF regardless of the R-R interval feature. This avoids the classification of irregular rhythms with valid P waves as AF. Another possibility is to examine the regularity of R-R-R intervals, so-called double-R-R intervals. R-R intervals which are irregular but recur with regularity can be characteristic of atrial bigeminy and not AF, whereas irregularly recurring irregular R-R intervals are characteristic of AF. In the example of FIG. 10a, irregular R-R intervals $R-R_1$ and $R-R_2$ are shown between R-waves 100 and 102 and R-waves 102 and 104, respectively. But this irregular rhythm recurs with regularity, as the succeeding interval is an $R-R_1$ interval between R-waves 104 and 106. An R-R-R interval analysis of $R-R_1$ and $R-R_2$ would reveal this regular irregularity. Such a regularly recurring irregular rhythm may be characteristic of atrial bigeminy and not AF. However in FIG. 10b, three different R-R intervals, $R-R_1$, $R-R_2$, and $R-R_3$, are seen to successively occur between R-waves 100-107. Such irregular irregularity is revealed by an R-R-R interval analysis with a decision to classify this arrhythmia as AF.

Figure 11:
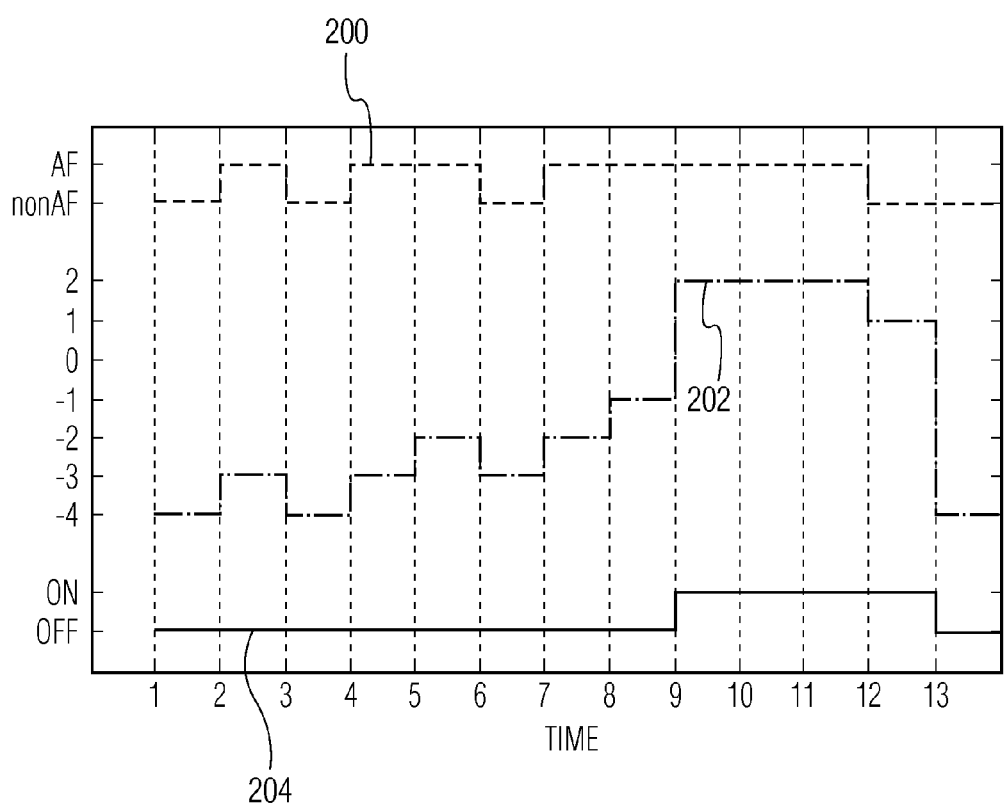
FIG. 11 illustrates a hysteresis counter which may be used to reduce false alarms.

A further reduction in false alarms is to implement a counter of AF episodes with built-in hysteresis. The hysteresis will eliminate alarms from short episodes of false positives and can be used to change the sensitivity and specificity of AF detection. FIG. 11 illustrates a non-symmetric counter (symmetric counters may also be used) which is configured to be less sensitive to the start of an AF episode than to the end of an AF episode. Such a counter will more definitively provide the user with notification that an AF episode has ended, which may play a role in the clinical diagnosis or therapy or drug regimen. In the example or FIG. 11, the upper step function 200 shows analysis intervals of multiple heartbeats which occur at times shown along the abscissa of the drawing and are classified as either AF or non-AF as indicated at the ordinate axis of the drawing. The counter is initialized in this example at a −4 level as shown by the start of counter steps 202, which plots the incrementing of the counter. Each interval classified as AF results in a step up of the counter (e.g., time 2) and each interval classified as non-AF steps the counter down (e.g., time 3). When the count of the counter reaches the zero threshold at time 9, it is incremented to the maximum count of +2 in this example, where it remains until non-AF intervals count it down. This begins at time 12 when a non-AF interval is counted. The next non-AF interval at time 13 counts the counter back to zero, at which time the counter is immediately reset to the initial −4 level. An alarm is issued whenever the count is above zero as shown by the alarm control 204 being ON at time 9 and turned OFF at time 13. This alarm control is seen to be less sensitive to AF episodes which would act to turn the alarm ON ("AF Begin"), and more sensitive to non-AF intervals which turn the alarm OFF ("AF End"). Different initial settings and thresholds for the counter will result in different hysteresis and hence different sensitivity and specificity to the issuing of an AF alarm or condition report to the user.

The output of the corrector 92 will report detected AF rhythms as shown in FIG. 6, which may be the AF/non-AF classifications of function 200, a false alarm limiting output such as alarm control function 204, or some other controlled AF decision process implemented by the user. The detected AF rhythms including the start time and end time of AF episodes are applied to an AF burden calculator 94 in FIG. 6 to report AF burden to the user. The calculated AF burden is a statistical calculation representing the frequency and duration of AF episodes. AF burden may also or alternatively be reported as the percentage of some previous time period (e.g., the past 24 hours or the complete monitored time) that the patient's heart has been in atrial fibrillation. AF burden is reported on the display or printer 28 and may be shown numerically, graphically, as a trend plot, or combinations thereof. The AF harden or the trend of the AF burden may be used by clinicians to guide future therapy or drug treatment for the patient.

What is claimed is:

1. An atrial fibrillation (AF) monitoring system comprising:
   a source of ECG waveform data;
   a P wave feature extractor;
   an R-R interval feature extractor;
   an AF classifier responsive to a P wave feature and an R-R interval feature which classifies a heart rhythm as AF or non-AF;
   a corrector responsive to the AF classifier for reclassifying a heart rhythm previously classified as AF by use of reclassification criteria;
   an atrial fibrillation alarm responsive to the AF classifier and the corrector for setting an AF Begin alarm at the beginning of an AF episode and an AF End alarm at the end of an AF episode;

an AF burden calculator responsive to heart rhythms classified as AF and the beginning and ending of an AF episode which calculates AF burden;

a display responsive to the AF burden calculator for reporting an AF burden calculation; and a user input for adjusting the sensitivity/specificity balance of AF rhythm detection, wherein the user input further comprises a selection of patient population type for automatically setting up a set of nominal AF rhythm detection parameters for the selected patient population type.

2. The atrial fibrillation (AF) monitoring system of claim 1, wherein the source of ECG waveform data comprises a beat classifier.

3. The atrial fibrillation (AF) monitoring system of claim 2, wherein the beat classifier produces a P wave template.

4. The atrial fibrillation (AF) monitoring system of claim 1, wherein the P wave feature extractor produces a P wave location feature and a P wave morphology feature.

5. The atrial fibrillation (AF) monitoring system of claim 4, wherein the AF classifier is responsive to a P wave location feature, a P wave morphology feature, and an R-R interval feature for classifying a heart rhythm as AF or non-AF.

6. The atrial fibrillation (AF) monitoring system of claim 4, wherein the P wave location feature comprises a P-Q or a P-R interval.

7. The atrial fibrillation (AF) monitoring system of claim 1, wherein the corrector is further responsive to an AF classification for reducing the occurrence of false alarms.

8. The atrial fibrillation (AF) monitoring system of claim 7, wherein the corrector is operable for measuring the irregularity of R-R intervals.

9. The atrial fibrillation (AF) monitoring system of claim 8, wherein the corrector is further operable to prevent alarms for short AF intervals by a hysteresis technique.

10. The atrial fibrillation (AF) monitoring system of claim 7, wherein the corrector is operable for identifying short AF intervals.

11. The atrial fibrillation (AF) monitoring system of claim 1, wherein the operation of the P wave feature extractor and the R-R interval feature extractor is subject to a noise estimation.

12. The atrial fibrillation (AF) monitoring system of claim 1, wherein the AF burden calculator reports the percentage of a time period that a heart rhythm has exhibited atrial fibrillation.

13. The atrial fibrillation (AF) monitoring system of claim 1, wherein the AF burden calculator reports the frequency and/or the duration of detected AF rhythm episodes.

* * * * *